(12) United States Patent
Kaji et al.

(10) Patent No.: US 9,340,630 B2
(45) Date of Patent: May 17, 2016

(54) METHOD FOR MANUFACTURING A SMALL PARTICLE DIAMETER PRODUCT OF SOLID POLYMETHYLALUMINOXANE COMPOSITION

(71) Applicant: Tosoh Finechem Corporation, Shunan, Yamaguchi (JP)

(72) Inventors: Eiichi Kaji, Shunan (JP); Etsuo Yoshioka, Shunan (JP)

(73) Assignee: TOSOH FINECHEM CORPORATION, Shunan, Yamaguchi (JP)

( * ) Notice: Subject to any disclaimer, the term of this patent is extended or adjusted under 35 U.S.C. 154(b) by 0 days.

(21) Appl. No.: 14/388,374

(22) PCT Filed: Mar. 15, 2013

(86) PCT No.: PCT/JP2013/057355
§ 371 (c)(1),
(2) Date: Sep. 26, 2014

(87) PCT Pub. No.: WO2013/146337
PCT Pub. Date: Oct. 3, 2013

(65) Prior Publication Data
US 2015/0057418 A1    Feb. 26, 2015

(30) Foreign Application Priority Data

Mar. 28, 2012 (JP) .................. 2012-072801

(51) Int. Cl.
| | | |
|---|---|---|
| *C08F 4/02* | (2006.01) | |
| *C08F 4/62* | (2006.01) | |
| *C08F 4/6592* | (2006.01) | |
| *C08F 110/02* | (2006.01) | |
| *C08F 4/659* | (2006.01) | |
| *C07F 5/06* | (2006.01) | |
| *C08G 79/10* | (2006.01) | |
| *C08L 85/00* | (2006.01) | |
| *C08F 10/00* | (2006.01) | |

(52) U.S. Cl.
CPC .............. *C08F 110/02* (2013.01); *C07F 5/061* (2013.01); *C08F 4/6592* (2013.01); *C08F 4/65912* (2013.01); *C08G 79/10* (2013.01); *C08L 85/00* (2013.01); *C08F 4/65925* (2013.01); *C08F 10/00* (2013.01); *Y10T 428/2982* (2015.01)

(58) Field of Classification Search
CPC .... C07F 5/061; C08F 6/65912; C08F 6/6592; C08F 10/00
See application file for complete search history.

(56) References Cited

U.S. PATENT DOCUMENTS

| | | | |
|---|---|---|---|
| 5,332,706 | A | 7/1994 | Nowlin et al. |
| 5,420,220 | A | 5/1995 | Cheruvu et al. |
| 5,473,028 | A | 12/1995 | Nowlin et al. |
| 5,602,067 | A | 2/1997 | Nowlin et al. |
| 5,608,019 | A | 3/1997 | Cheruvu et al. |
| 5,831,109 | A | 11/1998 | Smith et al. |
| 2007/0197745 | A1 | 8/2007 | Kaji et al. |
| 2011/0282017 | A1 | 11/2011 | Kaji et al. |

FOREIGN PATENT DOCUMENTS

| | | |
|---|---|---|
| EP | 2360191 A1 | 8/2011 |
| EP | 2570437 A1 | 3/2013 |
| JP | S63-198691 A | 8/1988 |
| JP | H07-42301 A | 2/1995 |
| JP | H07-70144 A | 3/1995 |
| JP | H07-300486 A | 11/1995 |
| JP | H08-319309 A | 12/1996 |
| JP | H09-504825 A | 5/1997 |
| JP | 2000-095810 A | 4/2000 |
| JP | 2005-263749 A | 9/2005 |
| WO | 9723288 A1 | 7/1997 |
| WO | 9818801 A1 | 5/1998 |
| WO | 02060908 A1 | 8/2002 |
| WO | 2010055652 A1 | 5/2010 |
| WO | 2011142400 A1 | 11/2011 |

OTHER PUBLICATIONS

Int'l Search Report issued May 28, 2013 in Int'l Application No. PCT/JP2013/057355.

(Continued)

*Primary Examiner* — Caixia Lu
(74) *Attorney, Agent, or Firm* — Panitch Schwarze Belisario & Nadel LLP (57) ABSTRACT

A solid polymethylaluminoxane composition is provided having uniform particle diameter in the form of fine particles of less than 5 μm employed to polymerize olefins with high polymerization activity without silica. A method for manufacturing thereof, a polymerization catalyst, and a method for manufacturing a polyolefin are also provided. The solid polymethylaluminoxane composition: has an aluminum content within a range of 36 mass % to 43 mass %; has a mole fraction of methyl groups derived from trimethylaluminum moieties relative to the total number of mols of methyl groups of 12 mol % or less; and is particulate having a median diameter based on volume within a range of 0.1 μm to less than 5 μm. In a step of heating an aromatic hydrocarbon solution containing trimethylaluminum and the poly¬ methylaluminoxane to cause solid poly¬ methyl¬ aluminoxane composition to precipitate, prior to or during the heat treating step, a dry, inert gas is bubbled through.

15 Claims, 1 Drawing Sheet

(56) References Cited

OTHER PUBLICATIONS

Int'l Preliminary Report on Patentability issued Oct. 09, 2014 in Int'l Application No. PCT/JP2013/057355.
Search Report and Examination Report issued Jun. 11, 2005 in Singapore Application No. 11201406100W.
Notice of Eligibility for Grant issued Jun. 30, 2015 in SG Application No. 11201406100W.
Extended EP Search Report issued Oct. 28, 2015 in EP App No. 13770307.0.
US 5,883,203, 03/1999, Cheruvu (withdrawn)

METHOD FOR MANUFACTURING A SMALL PARTICLE DIAMETER PRODUCT OF SOLID POLYMETHYLALUMINOXANE COMPOSITION

CROSS-REFERENCE TO RELATED APPLICATION

This application is a Section 371 of International Application No. PCT/JP2013/057355, filed Mar. 15, 2013, which was published in the Japanese language on Oct. 3, 2013, under International Publication No. WO 2013/146337 A1, and also claims benefit of priority to Japanese Patent Application No. 2012-72801, filed on Mar. 28, 2012, both of which are expressly incorporated herein by reference in their entity.

TECHNICAL FIELD

The present invention relates to a method for manufacturing a small particle diameter product of solid polymethylaluminoxane composition employed to polymerize olefins, to a polymerization catalyst employing the solid polymethylaluminoxane composition obtained as a catalyst component, and to a method for manufacturing a polyolefin.

BACKGROUND ART

Solutions of polyaluminoxane compositions are generally condensation products prepared by the partial hydrolysis of an organic aluminum compound, and are known to be useful as cocatalyst components for efficiently activating transition metal compounds serving as primary catalysts in the manufacturing of olefin polymers. Polymethylaluminoxane compositions employing trimethylaluminum as starting material organic aluminum compounds are widely known to exhibit particularly good cocatalyst performance. These compositions are normally handled in the form of solutions obtained by dissolving them in aromatic hydrocarbon solvents such as toluene.

Polymethylaluminoxane compositions exhibit good cocatalyst performance. However, because they are normally handled in the form of solutions obtained by dissolving both a primary catalyst such as a metallocene compound and a polymethylaluminoxane composition in a solvent, it is impossible to control the morphology of the polymer that is produced. Thus, not only does handling of the polymer become difficult, there is a problem in the form of a strong tendency for occurrence of fouling due to adhesion of the polymer to the polymerization reactor or the like.

The method of applying a support-type solid polymethylaluminoxane composition—in which a polymethylaluminoxane composition is supported on a solid inorganic support such as silica, alumina, or magnesium oxide—to suspension polymerization or gas phase polymerization has been proposed to solve these problems. Among the solid inorganic supports, silica in which the quantity of surface hydroxyl groups is controlled is the most widely employed as a support, with a number of examples of extension to the industrial level. (For example, see Patent Reference 6 and the like.)

The above silica support tends to remain within the polymer and is known to compromise the performance of the polymer. Further, solid polymethylaluminoxane compositions in which such supports are employed are known to exhibit a large drop in polymerization activity relative to the activity in homogeneous polymerization. Accordingly, to solve the above problem, it would be desirable to develop a solid polymethylaluminoxane composition with high activity rivaling that of homogeneous polymerization while retaining the merit of being solid of polymethylaluminoxane compositions as a cocatalyst.

Attempts have been made to obtain solid polymethylaluminoxane compositions without the use of solid supports such as those set forth above. Generally, when attempting to prepare a solid polymethylaluminoxane composition, the method of reacting some sort of additive with a solution of polymethylaluminoxane composition is adopted (see Patent References 1 to 5 and the like). However, in this method, the recovery ratio of solid material based on aluminum is not high.

In some cases, the addition of a third component to obtain a solid polymethylaluminoxane composition creates problems such as toxicity, depending on the use of the polymer. Such addition is thus better avoided. Due to such considerations, there have been proposed methods of obtaining solid polymethylaluminoxane compositions by adding just a solvent of non-solubility or poor-solubility to a solution of a polymethylaluminoxane composition. Patent References 1 and 5 propose methods of adding n-hexane or n-decane to a toluene solution of a polymethylaluminoxane composition to cause the solid polymethylaluminoxane composition to precipitate, and then increasing the amount of precipitation by removal of the solvent using a vacuum pump.

Although the yield and average particle diameter of the solid polymethylaluminoxane composition that precipitates are recorded in the methods set forth in Patent References 1 and 5, other than these, there is no mention of morphologies.

When combining a solid polymethylaluminoxane composition with a transition metal compound to prepare an olefin polymer, the properties of the olefin polymer being prepared are greatly influenced by the morphology of the solid polymethylaluminoxane composition. Generally, the solid polymethylaluminoxane composition with fine particles and a relatively uniform particle diameter is desirable because the olefin polymer that is prepared will have more uniform particles. The particle diameter of the solid polymethylaluminoxane composition described in the embodiments of Patent Reference 1 is 210 to 350 μm, and the particle diameter of the solid polymethylaluminoxane composition described in Patent Reference 5 is 28 to 47 μm. That is, in these patent references, there is no description of, and it is unclear, what must be done to prepare a solid polymethylaluminoxane composition with a small particle diameter of 30 μm or less. It is also unclear to what degree the particle diameter of the solid polymethylaluminoxane composition described in the embodiments is uniform.

There is also a problem in that a solid polymethylaluminoxane composition will generally have lower polymerization activity than a solution of polymethylaluminoxane composition. The yield of a solid polymethylaluminoxane composition is also low and the cost is high because the entire quantity of the polymethylaluminoxane contained in a solution of polymethylaluminoxane composition is not recovered as solid polymethylaluminoxane composition. When obtaining a solid polymethylaluminoxane composition such as by the methods described in Patent References 1 and 5, the method of removing a large amount of solvent from the solution of polymethylaluminoxane composition with a vacuum pump presents no problem and can be implemented at the lab level, but when considering implementation on an commercial scale, there is a possibility that polymethylaluminoxane or trimethylaluminum that does not solidify will scatter toward the vacuum pump. This is not only dangerous, but presents numerous problems from the perspective of production efficiency, and is not a practical way to conduct operations.

The present inventors recently discovered a solid polymethylaluminoxane composition with relatively fine particles with a median diameter based on volume falling within a range of 5 to 50 μm and with relatively uniform particle diameter, and a method for efficiently preparing the same (Patent Reference 7) without using a solid support such as SiO$_2$. The solid polymethylaluminoxane composition obtained in Patent Reference 7 is characterized not only by relatively fine particles of a particle diameter that is relatively uniform, but also by the fact that the polymerization activity is extremely high in the course of preparing an olefin polymer. Depending on the conditions, activity rivaling that of solution polymethylaluminoxane compositions is sometimes exhibited.

In this process, it is possible to provide a method such that the yield of polymethylaluminoxane composition in the process of preparing a solid polymethylaluminoxane composition from a solution of a polymethylaluminoxane composition is high and the removal of solvent by vacuum pump from the solution of polymethylaluminoxane composition is unnecessary.

PRIOR ART DOCUMENTS

Patent Documents

[Patent Document 1] Japanese Patent Un-Examined Publication 2000-95810
[Patent Document 2] Japanese Patent Un-Examined Publication Hei 8-319309
[Patent Document 3] Japanese Patent Un-Examined Publication Hei 7-300486
[Patent Document 4] Japanese Patent Un-Examined Publication Hei 7-70144
[Patent Document 5] Japanese Patent Examined Publication Hei 7-42301
[Patent Document 6] WO97/23288 (Japanese translation publication 2000-505785)
[Patent Document 7] WO2010/055652 (PCT/JP2009/006019)

Patent Documents 1 to 7 are expressly incorporated herein by reference in their entirety.

With the method described in Patent Reference 7, it was difficult to obtain a solid methylaluminoxane of fine particle diameter of less than 5 μm despite examining various synthesis conditions. Pulverization methods are sometimes utilized to form fine particles. However, when applied to the preparation of solid methylaluminoxane of fine particle diameter, not only do the particle diameters not align, but numerous particles with shapes like glass shards are formed. When such particles are used to polymerization, they tend to cause fouling to the reaction vessel, and their use is to be avoided.

Additionally, a further problem to be solved by the present invention is how to provide a method for industrially, efficiently, and inexpensively manufacturing a high-quality olefin polymer using the above fine particle diameter solid polymethylaluminoxane composition and a transition metal compound.

Means of Solving the Problem

To solve the above-stated problems, the present invention is as follows.

[1]
A solid polymethylaluminoxane composition:
(i) wherein the aluminum content falls within a range of 36 mass % to 43 mass %;
(ii) wherein the mole fraction of methyl groups derived from trimethylaluminum moieties relative to the total number of mols of methyl groups is 12 mol % or less; and
(iii) that is particulate, with the median diameter based on volume falling within a range of 0.1 μm to less than 5 μm.
[2]
The composition according to [1], wherein:
the solubility in n-hexane at 25° C. is 0 to 2 mol %; and
the solubility in toluene at 25° C. is 0 to 2 mol %.
[3]
The composition according to [1] or [2], wherein the uniformity as given by the following formula is 0.45 or lower:

uniformity=$\Sigma Xi|d(0.5)-Di|/d(0.5)\Sigma Xi$ (wherein Xi denotes the volume percentage of a particle i of solid aluminoxane composition in a particle diameter distribution histogram, d(0.5) denotes the median diameter based on volume in the histogram, and Di denotes the diameter based on volume of particle i in the histogram).
[4]
The composition of any one of [1] to [3], wherein the specific surface area falls within a range of 10 to 25 m$^2$/mmol-Al.
[5]
The composition according to any one of [1] to [4], comprising trimethyl aluminum and polymethylaluminoxane containing the unit denoted by general formula (I) below:

-[(Me)AlO]$_n$—　　　(I)

(wherein n denotes an integer of 10 to 50).
[6]
The composition according to any one of [1] to [5], not containing SiO$_2$.
[7]
A method for manufacturing the solid polymethylaluminoxane composition according to any one of [1] to [6], comprising a step (a) of heating an aromatic hydrocarbon solution containing trimethylaluminum and the polymethylaluminoxane containing the unit denoted by general formula (II) below (referred to hereinafter as the solution of polymethylaluminoxane composition) to cause solid polymethylaluminoxane composition containing trimethylaluminum and polymethylaluminoxane to precipitate;
wherein prior to step (a), a dry, inert gas is bubbled through the solution of polymethylaluminoxane composition, and/or during at least a portion of the period of step (a), a dry, inert gas is bubbled through the solution of polymethylaluminoxane composition:

-[(Me)AlO]$_n$—　　　(II)

(wherein n denotes an integer of 1 to 50).
[8]
The manufacturing method according to [8], wherein in the solution of polymethylaluminoxane composition prior to heating, the mole fraction of methyl groups derived from trimethylaluminum moieties relative to the total number of mols of methyl groups is 15 mol % or less.
[9]
The manufacturing method according to [8] or [9], wherein in step (a), a suitable heating temperature and heating period are selected from:

(i) heating temperatures falling within a range of 80 to 200° C. and
(ii) heating periods of from 5 minutes or more to less than 24 hours,
to cause the solid polymethylaluminoxane composition to precipitate.

[10]
The manufacturing method according to any one of [7] to [9], wherein the solution of polymethylaluminoxane composition employed as a starting material in step (a) is obtained by thermally decomposing an alkyl aluminum compound having an aluminum-oxygen-carbon bond.

[11]
The manufacturing method according to [10], wherein the alkyl aluminum compound having aluminum-oxygen-carbon bond is prepared by reacting trimethylaluminum and an oxygen-containing organic compound.

[12]
The manufacturing method according to [11], wherein the oxygen-containing organic compound is an aliphatic or aromatic carboxylic acid denoted by general formula (III):

$$R^1—(COOH)_n \quad (III)$$

(wherein $R^1$ denotes a hydrocarbon group in the form of a C1 to C20 linear or branched alkyl group, alkenyl group, or aryl group and n denotes an integer of 1 to 5).

[13]
The manufacturing method according to [11] or [12], wherein the reaction of the trimethylaluminum and oxygen-containing organic compound is conducted such that the molar ratio of aluminum atoms contained in the trimethylaluminum and oxygen atoms contained in the oxygen-containing compound falls within a range of 1.15 to 1.4:1.

[14]
An olefin polymerization catalyst comprising the solid polymethylaluminoxane composition according to any one of [1] to [6] and a catalyst component in the form of the transition metal compounds denoted by general formula (IV) below:

$$MR^5R^6R^7R^8 \quad (IV)$$

(wherein M denotes a transition metal element; $R^5$, $R^6$, $R^7$, and $R^8$ denote together organic groups comprising one or two cycloalkanedienyl skeletons, or each independently denote an organic group or atom selected from the group consisting of a hydrocarbon group with 1 to 20 carbon atoms, alkoxy group, aryloxy group, alkylsilyl group, alkylamide group, alkylimide group, alkylamino group, alkylimino group, hydrogen atom, and halogen atom).

[15]
A method for manufacturing a polyolefin, comprising polymerizing an olefin using the catalyst according to [14].

Effect of the Invention

The present invention makes it possible to obtain, with great convenience and high yield, a solid polymethylaluminoxane composition of uniform particle diameter in the form of fine particles of less than 5 μm. Extremely high polymerization activity is exhibited when the solid polymethylaluminoxane composition of the present invention is employed as a cocatalyst in polymerization. Further, the solubility in solvent of the solid polymethylaluminoxane composition of the present invention is extremely low. As a result, it is possible to greatly inhibit fouling of the reaction vessel when employed in polymerization, yielding a polymer of uniform particle diameter.

MODES OF CARRYING OUT THE INVENTION

[Solid Polymethylaluminoxane Composition]
The present invention is a solid polymethylaluminoxane composition:
(i) wherein the aluminum content falls within a range of 36 mass % to 43 mass %;
(ii) wherein the mole fraction of methyl groups derived from trimethylaluminum moieties relative to the total number of mols of methyl groups is 12 mol % or less; and
(iii) that is particulate, with the median diameter based on volume falling within a range of 0.1 μm to less than 5 μm.

The solid polymethylaluminoxane composition of the present invention contains polymethylaluminoxane and trimethylaluminum. The state in which the polymethylaluminoxane and trimethylaluminum are present together is not necessarily clear. However, the polymethylaluminoxane and trimethylaluminum are contained in a composition ratio and state that satisfy (i) and (ii) above.

The polymethylaluminoxane can contain the unit denoted by general formula (I) below, for example:

$$-[(Me)AlO]_n— \quad (I)$$

(wherein n denotes an integer of 10 to 50).

The term "contains the unit that is denoted by general formula (I)" means that it contains a polymethylaluminoxane in which n denotes a single number falling within the above range (n denotes a specific integer) or multiple types of polymethylaluminoxane (where n denotes multiple different integers). The fact that n denotes an integer of from 10 to 50 is based on the fact that the n of the polymethylaluminoxane in the solution of polymethylaluminoxane composition that is the raw material of the solid polymethylaluminoxane composition is 10 to 50. In the literature, it is described that disproportionation between the polymethylaluminoxane chains or between the polymethylaluminoxane chain and the trimethylaluminum in the solution of polymethylaluminoxane composition causes variation in the length of the polymethylaluminoxane chains. Trimethylaluminum is generated when the polymethylaluminoxane chains undergo disproportionation, and trimethylaluminum is consumed when polymethylaluminoxane chains and trimethylaluminum undergo disproportionation. However, when the solid polymethylaluminoxane was measured by $^1$H-NMR with $d_8$-THF as solvent prior to solvent washing, no pronounced change in the trimethylaluminum content appeared. Based on this fact, it was thought that the n of the polymethylaluminoxane in the solid polymethylaluminoxane composition was nearly equivalent to the n of the solution of polymethylaluminoxane composition employed as a starting material. The polymethylaluminoxane in the present invention, so long as it contains the above unit, can have a chainlike structure, cyclic structure, or branched structure.

When the polymethylaluminoxane has a cyclic structure, the theoretical level of the aluminum content is about 46 to 47 mass % and the theoretical level of the aluminum content in the trimethylaluminum is about 38 mass %. That is, in cases such as when the aluminum content in the solid polymethylaluminoxane composition exceeds 46 mass %, the solid polymethylaluminoxane composition is comprised only of polymethylaluminoxane having a cyclic structure, with little trimethylaluminum presumed to be present, and with no impurities such as solvent being contained. In cases when the polymethylaluminoxane has a linear structure, the theoretical level of the aluminum content varies with the number n in general formula (I), becoming smaller than in the case of a cyclic structure. Additionally, in the solid polymethylaluminoxane composition of the present invention, in addition to polymethylaluminoxane with a cyclic structure, polymethylaluminoxane having a linear structure and branched structure is contained. In addition to trimethylaluminum, impurities such as residual solvent are also contained. Thus, as indicated by (i), in the solid polymethylaluminoxane composition of the present invention, the aluminum content falls within a range of from 36 mass % to 43 mass %. The lower the aluminum content, the greater the abundance ratio of trimethylaluminum, and the higher the aluminum content, the smaller the abundance ratio of trimethylaluminum tends to be.

Keeping the aluminum content to within the range of from 36 mass % to 43 mass % imparts to the solid polymethylaluminoxane composition the properties of good uniformity of particle diameter and strength such that fracturing due to a tendency to crack does not occur. Conversely, an aluminum content in the present invention of less than 36 mass % is an indication of inadequate drying and the excessive incorporation of impurities such as solvent. When the aluminum content exceeds 43 mass %, as set forth above, the cyclic structure is presumed to be comprised primarily of polymethylaluminoxane, and it is an indication that neither trimethylaluminum nor solvent impurities are contained. However, the composition itself differs from the solid polymethylaluminoxane composition that is obtained by the present invention. From the above perspectives, the lower limit of the aluminum content is desirably 37 mass %, preferably 38 mass %, and the upper limit is desirably 42 mass %, preferably 41 weight percent. The range of the aluminum content is desirably from 38 mass % to 41 mass %.

The aluminum content of the solid aluminoxane composition and solution of polymethylaluminoxane composition that are prepared in the present invention can be determined, for example, by adding an excess quantity of disodium ethylene diamine tetracetate to a solution that has been hydrolyzed with 0.5 N sulfuric acid aqueous solution, and performing a reverse titration with zinc sulfate using dithizone as an indicator. When the measurement concentration is dilute, measurement can be conducted by atomic absorption spectrometry.

In the mole fraction of methyl groups derived from trimethylaluminum moieties relative to the total number of mols of methyl groups indicated by (ii), the total number of mols of methyl groups is the total number of mols of methyl groups derived from polymethylaluminoxane and methyl group derived from trimethylaluminum. The number of mols of methyl groups derived from trimethylaluminum moieties is the number of mols of methyl groups derived from trimethylaluminum. The mole fraction of methyl groups derived from trimethylaluminum moieties is 12 mol % or less. A low mole fraction of methyl groups derived from trimethylaluminum moieties means that there are few methyl groups derived from trimethylaluminum moieties contained in the polymethylaluminoxane, and that there is much aluminum in the form of polymethylaluminoxane chains. Keeping the mole fraction of methyl groups derived from trimethylaluminum moieties to 12 mol % or lower yields a solid polymethylaluminoxane composition with little solvent solubility and with strength to resist particle damage by the drying treatment. Conversely, when the mole fraction of methyl groups derived from trimethylaluminum moieties exceeds 12 mol %, solvent solubility rises and the particles tend to fracture readily.

The mole fraction of methyl groups derived from trimethylaluminum moieties in the solid methyl aluminoxane composition of the present invention is desirably 11 mol % or lower. The lower limit of the molar ratio of methyl groups derived from trimethylaluminum moieties is, for example, desirably 6 mol % and preferably 8 mol % because it depends on the solution of polymethylaluminoxane serving as a starting material permitting control of the shape of the solid polymethylaluminoxane.

The polymethylaluminoxane composition that is employed in the present invention contains unreacted starting material in the form of internal trimethylaluminum. In the present invention, the quantity of trimethylaluminum that is present in the polymethylaluminoxane composition is denoted as the mole fraction of the methyl groups derived from polymethylaluminoxane and trimethylaluminum (denoted as Me(PMAO) and Me(TMAL), respectively).

The mole fractions of the various components in the polymethylaluminoxane composition can be determined based on the integrated peak area on the ratios assigned to the various components based on $^1$H-NMR measurement of the polymethylaluminoxane composition. Examples of the specific method of determining the Me(PMAO) and Me(TMAL) mole fractions of a polymethylaluminoxane composition are given in the embodiments.

The solid polymethylaluminoxane composition of the present invention is particulate and desirably has a uniformity of 0.45 or less as given by the equation below:

$$\text{uniformity} = \Sigma Xi|d(0.5)-Di|/d(0.5)\Sigma Xi$$

(wherein Xi denotes the volume percentage of a particle i of solid aluminoxane composition in a particle diameter distribution histogram, d(0.5) denotes the median diameter based on volume in the histogram, and Di denotes the diameter based on volume of particle i in the histogram).

By keeping the uniformity of the particulate solid polymethylaluminoxane composition of the present invention to 0.45 or lower, it is possible to obtain an olefin polymer with an uniform particle diameter using the solid polymethylaluminoxane composition and a transition metal compound. The uniformity is desirably 0.4 or less, preferably 0.35 or less, and more preferably, 0.3 or less. The lower the value of the homogeneity, the more uniform the particle diameters of the particles of olefin polymer obtained tend to be. The uniformity is employed as an indicator of catalyst particle diameter distribution. The greater the value of the indicator, the broader the distribution indicated. Taking into account that the particle shape is controlled by means of self-association of the solid polymethylaluminoxane composition, the lower limit of uniformity can be 0.15.

The solid polymethylaluminoxane composition of the present invention can be prepared as a particulate composition with a median diameter based on volume falling within a range of from 0.1 μm to less than 5 μm. Keeping the median diameter based on volume of the particulate solid polymethylaluminoxane composition of the present invention within the above range maintains a good polymer bulk density using the solid polymethylaluminoxane composition and transition metal component, and yields an olefin polymer in which the generation of micropowder polymer is inhibited. From the perspective of achieving good particle properties such as bulk density in the olefin polymer that is obtained, it generally suffices for the median diameter based on volume of the solid polymethylaluminoxane composition to be about 5 to 200 μm. However, a fine particulate product of less than 5 μm is desirable to extend use to the formation of uniform polymers on the surfaces of materials by spraying a liquid in which the catalyst has been suspended and passing an olefin gas. Accordingly, taking into account uniformity, the median diameter based on volume of the solid polymethylaluminoxane composition of the present invention is desirably 0.1 µm to less than 5 µm, preferably falling within a range of 0.1 to 4 µm, more preferably falling within a range of 0.1 to 3 µm, still more preferably falling within a range of 0.1 to 2 µm, and yet more preferably, falling within a range of 0.1 to 1 µm.

The median diameter based on volume and the particle diameter distribution of the solid polymethylaluminoxane composition of the present invention can be determined by the laser diffraction/scattering method under a dry nitrogen atmosphere using a Master Sizer 2000 Hydro S made by Malvern Instruments Ltd. The specific methods are described in the embodiments.

The solid polymethylaluminoxane composition of the present invention is desirably particulate with a specific surface area falling within a range of 10 to 25 m$^2$/mmol-Al. Keeping the specific surface area of the particulate solid polymethylaluminoxane composition of the present invention to within this range affords good activity in the polymerization of an olefin compound using the solid polymethylaluminoxane composition and transition metal compound. Here, the term "good activity" desirably means the same activity as that obtained when employing a solution of polymethylaluminoxane composition. However, the good polymerization activity of the solid polymethylaluminoxane composition of the present invention does not depend just on the specific surface area, but can be considered to also depend on the composition and structure in addition to the specific surface area of the solid polymethylaluminoxane composition. The specific surface area could conceivably affect activation caused by contact of the catalyst of the transition metal compound, including the metallocene compound serving as the primary catalyst, with the solid polymethylaluminoxane composition in the course of employing them to polymerize an olefin. That is, when the specific surface area is small, the activation efficiency of the primary catalyst generally deteriorates, and when it is large, the activation efficiency is thought to be high. Additionally, when the specific surface area is excessively high, the interior of the solid polymethylaluminoxane composition becomes excessively porous and the strength of the solid is thought to diminish. For these reasons, the range is desirably 10 to 25 m$^2$/mmol-Al, preferably 13 to 22 m$^2$/mmol-Al.

The specific surface area of the solid polymethylaluminoxane composition of the present invention can be determined by utilizing the gas adsorption phenomenon in solid surfaces with the BET adsorption isotherm. The specific method is described in the embodiments.

The solubility of solid polymethylaluminoxane composition of the present invention in n-hexane at 25° C. is 0 to 2 mol % and the solubility in toluene at 25° C. is desirably 0 to 2 mol %.

The solid polymethylaluminoxane composition of the present invention is characterized by the fact that the proportion dissolving in n-hexane or toluene when maintained at 25° C. is extremely low. For n-hexane, this proportion falls within a range of 0 to 2 mol %, desirably 0 to 1 mol %, and preferably, 0 to 0.2 mol %. For toluene, this proportion falls within a range of 0 to 2 mol %, desirably 0 to 1 mol %, and preferably, 0 to 0.5 mol %. The ratio of dissolution in solvent can be measured by implementing the method described in Japanese Examined Patent Publication (KOKOKU) Heisei No. 7-42301. A specific description is given in the embodiments.

The solid polymethylaluminoxane composition of the present invention does not contain SiO$_2$. In at least the process of manufacturing the solid polymethylaluminoxane composition of the present invention, no SiO$_2$ is actively incorporated. Because the solid polymethylaluminoxane composition of the present invention does not contain SiO$_2$, the drawbacks of solid polymethylaluminoxane compositions containing SiO$_2$ are avoided.

[The Method for Manufacturing a Solid Polymethylaluminoxane Composition]

The method for manufacturing a solid polymethylaluminoxane composition of the present invention comprises a step (a) of heating an aromatic hydrocarbon solution containing trimethylaluminum and the polymethylaluminoxane containing the unit denoted by general formula (II) below (the solution of polymethylaluminoxane composition) to cause solid polymethylaluminoxane composition containing trimethylaluminum and polymethylaluminoxane to precipitate; wherein prior to step (a), a dry, inert gas is bubbled through the solution of polymethylaluminoxane composition, and/or during at least a portion of the period of step (a), a dry, inert gas is bubbled through the solution of polymethylaluminoxane composition:

-[(Me)AlO]$_n$—     (II)

(wherein n denotes an integer of 10 to 50).

"Containing the unit denoted by general formula (II)" means containing polymethylaluminoxane in which n denotes a single number falling within the above range (n denotes a specific integer) or multiple types of polymethylaluminoxane (where n denotes multiple different integers). The fact that n denotes an integer of 10 to 50 is based on the fact that the degree of polymerization of aluminoxane based on the molecular weight obtained from of freezing point depression in benzene is within the range of 10 to 50.

The solution of polymethylaluminoxane composition that is employed as a starting material in the manufacturing method of the present invention can be prepared, for example, by the method described in Patent Reference 6. The method described in Patent Reference 6 is a method of preparing a polymethylaluminoxane composition without hydrolyzing trimethylaluminum. Specifically, it is a method of obtaining a solution of polymethylaluminoxane composition by thermally decomposing an alkyl aluminum compound having aluminum-oxygen-carbon bonds.

Examples of the aromatic hydrocarbon that is employed in the solution of polymethylaluminoxane composition are: benzene, toluene, ethyl benzene, propyl benzene, butyl benzene, xylene, chlorobenzene, and dichlorobenzene. However, there is no limitation to these examples. Any aromatic hydrocarbon can be employed as the solvent in the solution of polymethylaluminoxane composition.

The alkyl aluminum compound having an aluminum-oxygen-carbon bond is desirably prepared by reacting trimethylaluminum with an oxygen-containing organic compound. The oxygen-containing organic compound is desirably an aliphatic or aromatic carboxylic acid denoted by general formula (III):

R$^1$—(COOH)$_n$     (III)

(wherein R$^1$ denotes a hydrocarbon group in the form of a C1 to C20 linear or branched alkyl group, alkenyl group, or aryl group and n denotes an integer of 1 to 5).

The oxygen-containing compound employed in the reaction of an oxygen-containing compound and trimethylaluminum to obtain an alkyl aluminum compound having an aluminum-oxygen-carbon bond that yields a solution of polymethylaluminoxane composition through a thermal decomposition reaction is, for example, a carboxylic anhydride or a carboxylic acid compound having a COOH group. One or more of these compounds can be employed to prepare the solution of polymethylaluminoxane composition. Specific examples of oxygen-containing compounds are formic acid, acetic acid, propionic acid, n-butyric acid, n-valeric acid, n-caproic acid, n-enanthic acid, n-caprylic acid, n-pelargonic acid, n-capric acid, n-lauric acid, n-myristic acid, n-stearic acid, oxalic acid, malonic acid, succinic acid, glutaric acid, adipic acid, pimelic acid, suberic acid, azelaic acid, sebacic acid, benzoic acid, phthalic acid, citric acid, tartaric acid, lactic acid, malic acid, toluic acid, toluic anhydride, acetic anhydride, propionic anhydride, n-butyric anhydride, n-valeric anhydride, n-caproic anhydride, oxalic anhydride, malonic anhydride, succinic anhydride, glutaric anhydride, benzoic anhydride, phthalic anhydride, and toluic anhydride. Of these, acetic acid, acetic anhydride, propionic acid, propionic anhydride, benzoic acid, benzoic anhydride, phthalic acid, phthalic anhydride, toluic acid, and toluic anhydride are desirable.

The molar ratio of the aluminum atoms contained in the trimethylaluminum and the oxygen atoms of the oxygen-containing organic compound used in the synthesis of the solution of polymethylaluminoxane composition can, be set as desired with the goal of controlling the residual quantity of trimethylaluminum or the molecular weight of the polymethylaluminoxane. The ratio of the molar quantities of the aluminum atoms contained in the trimethylaluminum to the oxygen atoms of the oxygen-containing organic compound can be set anywhere within the range of 0.5 to 3.0:1.

From the perspectives of the ease of preparation and stability of the solution of the polymethylaluminoxane composition and suitable control of the quantity of residual trimethylaluminum, the ratio of the above molar quantities desirably falls within a range of 1.0 to 1.7:1, preferably within a range of 1.15 to 1.4:1.

The aluminum compound having an aluminum-oxygen-carbon bond that is the precursor of the solution of polymethylaluminoxane composition can be thermally decomposed at any temperature between 20 and 90° C. From the perspectives of the ease of handling and the stability of the reaction and a suitable reaction time, this temperature is desirably 30 to 80° C., preferably 60 to 80° C. The period of thermal decomposition of the aluminum compound having an aluminum-oxygen-carbon bond will vary with the thermal decomposition temperature and starting material composition (for example, the Al/O molar ratio). By way of example, it falls within a range of 5 to 100 hours. When the temperature is low, a long period is required. When the temperature is high, thermal decomposition can be completed in a short period.

A thermal decomposition temperature exceeding 100° C. triggers marked gelling and a decrease in the yield of uniform polymethylaluminoxane solution. Additionally, a thermal decomposition temperature that is lower than 50° C. will sometimes trigger a marked decrease in productivity due to an increase in the reaction time for producing polymethylaluminoxane.

In the present invention, it is important to control the temperature during preparation of the solution of polymethylaluminoxane composition used as a starting material. At first glance, a portion of the present invention might be understood as lying in the step of preparing a solution of polymethylaluminoxane composition. However, when attempting to obtain a solid polymethylaluminoxane composition of controlled particle diameter, it is impossible to directly obtain a solid polymethylaluminoxane composition without first obtaining a solution of polymethylaluminoxane composition by thermally decomposing an alkyl aluminum compound having an aluminum-oxygen-carbon bond that is a starting material of the solution of polymethylaluminoxane composition. Only by first thermally decomposing an alkyl aluminum compound containing an aluminum-oxygen-carbon bond to prepare a solution of polymethylaluminoxane composition and then heating under prescribed conditions the solution of polymethylaluminoxane composition that has been prepared is it possible to obtain a solid polymethylaluminoxane composition. For example, even when the solution of polymethylaluminoxane composition starting material is directly heated to 100° C., it is impossible to obtain a solid polymethylaluminoxane composition of uniform particle diameter. The reason for this is currently unclear. However, when the formation by heat treatment of a solid polymethylaluminoxane composition of energetically stable particle diameter by the self-association of polymethylaluminoxane having a certain chain length and chain length distribution is considered, the present inventors believe that it is possible to understand why a polymethylaluminoxane structure that has been properly formed is required.

It suffices for the polymethylaluminoxane concentration in the inert hydrocarbon to fall within a range of 6 to 40 mass %, desirably 6 to 30 mass %, and preferably, 10 to 25 mass %.

In most of the literature to date on obtaining a solution of a polymethylaluminoxane composition by the thermal decomposition reaction of an aluminum compound having an aluminum-oxygen-carbon bond, the focus has been on obtaining solutions of polymethylaluminoxane compositions at quantitative reaction yields and on the ability to control the amount of trimethylaluminum in the solution-type polymethylaluminoxane composition. Since trimethylaluminum generally does not function as an activating agent for transition metal compounds including metallocene compounds, controlling the amount of trimethylaluminum remaining in the solution of polymethylaluminoxane composition has been an important issue. Additionally, when preparing a solution of polymethylaluminoxane composition by the hydrolysis method, the aluminum recovery rate is known to decrease greatly unless the aluminum concentration in the reaction solution is kept low and the quantity of water introduced relative to the starting material trimethylaluminum is kept low.

In the solution of polymethylaluminoxane composition that is employed as a starting material, it is desirable for the mole fraction of methyl groups derived from trimethylaluminum moieties relative to the total number of moles of methyl groups to be 15 mol % or less from the perspective of increasing the yield of solid polymethylaluminoxane composition. The mole fraction of methyl groups derived from trimethylaluminum moieties relative to the total number of moles of methyl groups is desirably 14 mol % or less. The lower limit of the mole fraction of methyl groups derived from trimethylaluminum moieties relative to the total number of moles of method groups is 6 mol %. In the solution of polymethylaluminoxane composition prepared by the hydrolysis method, the mole fraction of methyl groups derived from aluminoxane moieties relative to the total number of moles of methyl groups is 40 to 50 mol %. It is difficult to lower the mole fraction of methyl groups derived from aluminoxane moieties relative to the total number of moles of methyl groups in a polymethylaluminoxane composition to 15 mol % or lower by the usual concentration and drying treatments. Additionally, in the preparation of a solution of polymethylaluminoxane composition by the thermal decomposition method, keeping the molar ratio of aluminum atoms contained in the trimethylaluminum and oxygen atoms in the oxygen-containing organic compound to 1.15 makes it possible to keep the lower limit of the mole fraction of methyl groups derived from aluminoxane moieties relative to the total number of moles of methyl groups to 8 mol %, and to achieve good performance in the solid polymethylaluminoxane composition that is obtained. Keeping the molar ratio of the aluminum atoms in the trimethylaluminum and the oxygen atoms in the oxygen-containing organic compound to 1.10 makes it possible to achieve a mole fraction of methyl groups derived from trimethylaluminum moieties relative to the total number of moles of methyl groups to 5.2 mol %. However, the performance of the solid polymethylaluminoxane composition that is obtained is poor. For these reasons, 8 to 14 mol % is desirable.

The aromatic hydrocarbon that is employed in the manufacturing method of the present invention is not specifically limited. Examples are benzene, toluene, ethylbenzene, propylbenzene, butylbenzene, xylene, chlorobenzene, and dichlorobenzene.

In step (a), a suitable heating temperature and heating period are selected from:
(i) heating temperatures falling within a range of 80 to 200° C. and
(ii) heating periods of from 5 minutes or more to less than 24 hours,
to cause the solid polymethylaluminoxane composition to precipitate.

The present inventors discovered that when the aromatic hydrocarbon solution containing the polymethylaluminoxane containing the unit shown in general formula (II) and trimethylaluminum (the solution of polymethylaluminoxane composition) was continuously heated at a prescribed temperature, the solid polymethylaluminoxane composition containing polymethylaluminoxane and trimethylaluminum precipitated into the solution in the form of uniform particle diameters. The term "prescribed temperature" is a range of from 80 to 200° C. The time required for precipitation varies with the temperature, and by way of example, falls within a range of from 5 minutes or more to less than 24 hours. Keeping it within this range makes it possible to obtain a solid polymethylaluminoxane composition of desired particle diameter and uniformity of particle diameter at a high yield. However, depending on the heating temperature, there are cases where heating for a period exceeding this range may be suitable. Precipitation of the solid polymethylaluminoxane composition into the solution increases with the elapse of time. Once a certain level has been reached, there is no further increase in the quantity of precipitating material. The amount of precipitating material (recovery rate) varies with the composition of the solution of polymethylaluminoxane composition and the concentration of the solute in the solvent (aromatic hydrocarbon solution).

Prior to step (a), a dry, inert gas is bubbled through the solution of polymethylaluminoxane composition or during at least some portion of the period of step (a), a dry, inert gas is bubbled through the solution of polymethylaluminoxane composition; or prior to step (a), a dry, inert gas is bubbled through the solution of polymethylaluminoxane composition and during at least some portion of the period of step (a), a dry, inert gas is bubbled through the solution of polymethylaluminoxane composition. The present inventors discovered that the bubbling of a dry, inert gas in the course of heating the solution of polymethylaluminoxane composition in this manner reduced the particle diameter of the solid polymethylaluminoxane composition that was produced. Here, the term "dry, inert gas" generally means nitrogen, helium, or argon gas. The term "dry gas" means a gas with a dew point of −65° C. or lower. In the bubbling, for example, the gas can be supplied through a mass flow meter by means of a dip tube inserted into the solution of polymethylaluminoxane composition. When conducting bubbling in advance, the gas supply rate is desirably set to within a range of from 100 mL/min to 2 L/min per one liter of solution of polymethylaluminoxane. This range is preferably from 500 mL/min to 1.5 L/min. Remaining within this range makes it possible to achieve the effect of efficiently reducing the particle diameter. When this range is exceeded, although also depending on the shape of the reaction vessel, scattering of the solution of polymethylaluminoxane solution onto the upper portion of the reaction vessel and escaping of the solvent toluene along with the gas become marked. In some cases, it becomes difficult to control the particle diameter. The supply period can be set to within a range of from 10 minutes to 2 hours. Desirably, it falls within a range of from 10 minutes to 1 hour. When this range is further reduced, it becomes difficult to achieve the small particle diameter effect. When long, escape of the solvent toluene along with the gas becomes pronounced and control of the particle diameter becomes difficult.

When bubbling is conducted during the heating reaction, the gas supply rate is desirably set to within a range of from 1 mL/min to 50 mL/min, preferably 1 mL/min to 10 mL/min, and more preferably, 1 mL/min to 5 mL/min, per liter of solution polymethylaluminoxane. When blowing gas in during heating, the gas itself is desirably heated in advance to a temperature corresponding to the temperature of the heating reaction. The gas is supplied for the period during which the solution of polymethylaluminoxane is being heat treated.

Taking into account the particle diameter, particle diameter uniformity, yield, and the like of the particles of solid polymethylaluminoxane composition, a heating temperature of 80 to 200° C. suffices, 90 to 150° C. is desirable, and 100 to 130° C. is preferred. At this temperature range, the time is desirably 1 to 20 hours, preferably 5 to 12 hours. However, when the temperature decreases, the time required for particles of solid polymethylaluminoxane composition to precipitate out increases. When the temperature is increased, the time required for particles of solid polymethylaluminoxane composition to precipitate out tends to decrease.

[The Olefin Polymerization Catalyst]

The present invention includes an olefin polymerization catalyst. The olefin polymerization catalyst of the present invention comprises the above solid polymethylaluminoxane composition of the present invention and a catalyst component in the form of the transition metal compounds denoted by general formula (IV) below:

$$MR^5R^6R^7R^8 \qquad (IV)$$

(wherein M denotes a transition metal element; $R^5$, $R^6$, $R^7$, and $R^8$ denote together organic groups comprising one or two cycloalkanedienyl skeletons, or each independently denote an organic group or atom selected from the group consisting of a hydrocarbon group with 1 to 20 carbon atoms, alkoxy group, aryloxy group, alkylsilyl group, alkylamide group, alkylimide group, alkylamino group, alkylimino group, hydrogen atom, and halogen atom).

The solid polymethylaluminoxane composition of the present invention can be combined with a known olefin polymerization catalyst for use as polymerization catalysts. Examples of olefin polymerization catalysts are transition metal compounds. These transition metal compounds can be those shown in general formula (IV) above.

Specific examples of M in general formula (IV) are titanium, zirconium, hafnium, chromium, vanadium, manganese, iron, cobalt, nickel, and palladium. Titanium, zirconium, chromium, iron, and nickel are desirable.

In general formula (IV), as a desirable transition metal compound, $R^5$, $R^6$, $R^7$, and $R^8$ can jointly constitute a compound exhibiting organic groups having one or two cycloalkadienyl skeletons, that is, a metallocene compound that is coordinated with one or two ligands having cycloalkadienyl skeletons. Examples of ligands having cycloalkadienyl skeletons are cyclopentadienyl groups, methyl cyclopentadienyl groups, ethyl cyclopentadienyl groups, butyl cyclopentadienyl groups, dimethyl cyclopentadienyl groups, pentamethyl cyclopentadienyl groups, other alkyl-substituted cyclopentadienyl groups, indenyl groups, and fluorenyl groups. The cycloalkadienyl groups can be crosslinked with divalent substituted alkylene groups, substituted silylene groups, or the like.

Ligands other than ligands having cycloalkadienyl skeletons are hydrocarbon groups with 1 to 20 carbon atoms, alkoxy groups, aryloxy groups, alkylsilyl groups, alkylamide groups, alkylimide groups, alkylamino groups, alkylimino groups, halogen atoms, and hydrogen atoms. This is the case where each of $R^5$, $R^6$, $R^7$, and $R^8$ independently denotes an organic group or atom selected from the group consisting of hydrocarbons having 1 to 20 carbon atoms, alkoxy groups, aryloxy groups, alkylsilyl groups, alkylamide groups, alkylimide groups, alkylamino groups, alkylimino groups, hydrogen atoms, and halogen atoms. The number of carbon atoms of hydrocarbon residues such as alkyl groups in groups containing hydrocarbon groups such as alkyl groups other than the above hydrocarbon groups having 1 to 20 carbon atoms (alkoxy groups, aryloxy groups, alkylsilyl groups, alkylamide groups, alkylimide groups, alkylamino groups, and alkylimino groups) can fall within a range of 1 to 20.

Examples of hydrocarbon groups with 1 to 20 carbon atoms are alkyl groups, cycloalkyl groups, aryl groups, and aralkyl groups. Specific examples of alkyl groups are methyl groups, ethyl groups, propyl groups, isopropyl groups, and butyl groups. Specific examples of cycloalkyl groups are cyclopentyl groups and cyclohexyl groups. Specific examples of aryl groups are phenyl groups and tolyl groups. A specific example of an aralkyl group is a benzyl group. Special examples of alkoxy groups are methoxy groups, ethoxy groups, and butoxy groups. A specific example of an aryloxy group is a phenoxy group. These groups can be substituted with halogen atoms and the like. Specific examples of alkylsilyl groups are trimethylsilyl groups and triethylsilyl groups. Specific examples of halogen groups are fluorine, chlorine, bromine, and iodine.

Specific examples of transition metal compounds containing ligands having cycloalkadienyl skeletons for the case where M in general formula (IV) denotes zirconium are: bis(cyclopentadienyl)zirconium monochloride monohydride, bis(cyclopentadienyl)zirconium monobromide monohydride, bis(cyclopentadienyl)methylzirconium hydride, bis(cyclopentadienyl)ethylzirconium hydride, bis(cyclopentadienyl)phenylzirconium hydride, bis(cyclopentadienyl)benzylzirconium hydride, bis(cyclopentadienyl)neopentylzirconium hydride, bis(methylcyclopentadienyl)zirconium monochloride hydride, bis(indenyl)zirconium monochloride hydride, bis(cyclopentadienyl)zirconium dichloride, bis(cyclopentadienyl)zirconium dibromide, bis(cyclopentadienyl)methylzirconium monochloride, bis(cyclopentadienyl)ethylzirconium monochloride, bis(cyclopentadienyl)cyclohexylzirconium monochloride, bis(cyclopentadienyl)phenylzirconium monochloride, bis(cyclopentadienyl)benzylzirconium monochloride, bis(methylcyclopenta-dienyl)zirconium dichloride, bis(dimethylcyclopentadienyl)zirconium dichloride, bis(n-butylcyclopentadienyl)zirconium dichloride, bis(indenyl)zirconium dichloride, bis(indenyl)zirconium dibromide, bis(cyclopentadienyl)zirconium dimethyl, bis(cyclopentadienyl)zirconium diphenyl, bis(cyclopentadienyl)zirconium dibenzyl, bis(cyclopentadienyl)zirconium monomethoxymonochloride, bis(cyclopentadienyl)zirconium monoethoxymonochloride, bis(methylcyclopenta-dienyl)zirconium monoethoxymonochloride, bis(cyclopentadienyl)zirconium monophenoxymonochloride, and bis(fluorenyl)zirconium dichloride.

Specific examples of transition metal compounds when M in general formula (IV) above is zirconium, containing at least two ligands having cycloalkadienyl skeletons, with the at least two ligands having cycloalkadienyl skeletons being bonded through alkylene groups such as ethylene or propylene, substituted alkylene groups such as isopropylidene and diphenylmethylene, or silylene or substituted silylene groups such as dimethylsilylene, are: ethylene bis(indenyl)dimethyl zirconium, ethylene bis(indenyl)diethyl zirconium, ethylene bis(indenyl)diphenyl zirconium, ethylene bis(indenyl)methylzirconium monochloride, ethylene bis(indenyl)ethylzirconium monochloride, ethylene bis(indenyl)methylzirconium monobromide, ethylene bis(indenyl)zirconium dichloride, ethylene bis(indenyl)zirconium bromide, and ethylene bis(4,5,6-tetrahydro-1-indenyl)zirconium dichloride. These can be racemic or meso forms, or a mixture thereof.

In uniform system polymerization, it suffices to use just one of these transition metal compounds. To adjust the atomic weight distribution and the like, two or more can be employed. When preparing a solid catalyst in advance, a single one of these transition metal compounds can be employed, or two or more can be employed to adjust the molecular weight distribution or the like.

[The Method for Manufacturing a Polyolefin]

The present invention includes a method for manufacturing a polyolefin comprising polymerizing an olefin using the above catalyst of the present invention.

In heterogeneous polymerization employing the solid polymethylaluminoxane composition of the present invention and in polymerization employing a supported catalyst prepared using the solid polymethylaluminoxane composition of the present invention, suitable performance is achieved in various methods adopting forms of polymerization such as solution polymerization employing a solution, bulk polymerization not employing a solvent, and gas phase polymerization. In both the methods of continuous polymerization and batch polymerization, desirable performance is achieved and molecular weight-adjusting agents such as hydrogen can be employed as needed.

With regard to the monomer employed in polymerization, any type of compound that can be employed as a single olefin monomer or combination thereof that can be employed in a copolymer will do. Specific examples are: ethylene, propylene, 1-butene, 1-pentene, 1-hexene, 1-decene, 1-hexadecene, 1-octadecene, 1-eicosene, other α-olefins, bisfluoroethylene, trifluoroethylene, tetrafluoroethylene, hexafluoropropene, other halogen-substituted olefins, cyclopentene, cyclohexene, norbornene, and other cyclic olefins.

EMBODIMENTS

The present invention is described in greater detail below through embodiments. However, the present invention is not limited to the embodiments.

In the embodiments set forth below, the solid polymethylaluminoxane composition is normally dried under a full vacuum generated by a vacuum pump at 40° C. via a seal pot charged with liquid paraffin, with drying being ended at the point where no bubbles are observed in the sealed pot.

[Test Methods]

(1) Solubility

The proportions of the solid polymethylaluminoxane composition of the present invention that dissolved in n-hexane and toluene maintained at a temperature of 25° C. was measured by the method described in Japanese Examined Patent Publication (KOKOKU) Heisei No. 7-42301. Specifically, the proportion of dissolution in n-hexane was determined by adding 2 g of the solid polymethylaluminoxane composition to 50 mL of n-hexane maintained at 25° C., stirring the mixture for 2 hours, using a membrane filter to separate the solution components, and measuring the concentration of aluminum in the filtrate. The dissolution proportion obtained by this method was determined as the proportion of aluminum atoms present in the filtrate relative to the number of aluminum atoms corresponding to 2 g of the solid polymethylaluminoxane composition employed as the sample.

(2) The Aluminum Content

The aluminum contents of the solution of polymethylaluminoxane composition and the solid polymethylaluminoxane composition were basically determined by adding an excess quantity of disodium ethylene diamine tetraacetate to a solution that had been hydrolyzed with a 0.5N sulfuric acid aqueous solution, and then conducting reverse titration with zinc sulfate using dithizone as indicator. In cases where dilute concentrations were measured, measurements were made by atomic absorption spectrometry.

(3) The Specific Surface Area of the Solid Polymethylaluminoxane Composition

The specific surface area of the solid polymethylaluminoxane composition was determined using the BET adsorption isotherm by exploiting the phenomenon of gas adsorption in solid surfaces. A BELSORP Mini II, made by BEL JAPAN, INC., was employed as the measurement device, and nitrogen gas was employed as the measurement gas.

(4) The Median Diameter Based on Volume and Particle Diameter Distribution of the Solid Polymethylaluminoxane Composition The median diameter based on volume and particle diameter distribution of the solid polymethylaluminoxane composition were determined by the laser diffraction/scattering method in a dry nitrogen atmosphere using a 2000 Hydro S Master Sizer from Malvern Instruments, Ltd. Primarily dehydrated, degassed n-hexane was employed as the dispersing agent. Dehydrated and degassed toluene sometimes is employed based on the objective. As an indicator of catalyst particle diameter distribution, the uniformity, defined as per the equation given below, was employed:

uniformity=$\Sigma Xi|d(0.5)-Di|/d(0.5)\Sigma Xi$ where Xi denotes the volume percentage of a particle i of solid aluminoxane composition in a particle diameter distribution histogram, d(0.5) denotes the median diameter based on volume in the histogram, and Di denotes the diameter based on volume of particle i in the histogram.

(5) The Mole Fraction of Methyl Groups

The mole fraction of each of the components in the polymethylaluminoxane composition was determined based on the surface area ratio assigned to the component based on $^1$H-NMR measurement of the polymethylaluminoxane composition. The specific methods of determining the mole fractions of Me(PMAO) and Me(TMAL) in the polymethylaluminoxane composition are set forth further below. The mole fraction of methyl groups derived from polymethylaluminoxane is denoted as Me(PMAO). The mole fraction of methyl groups derived from trimethyl aluminum is denoted as Me(TMAL).

First, $^1$H-NMR of a polymethylaluminoxane composition was measured using $d_8$-THF as a duterated solvent. The $^1$H-NMR measurement was conducted with a 300 MHz Gemini 2000 NMR measurement device from Varian Technologies Japan, Ltd. at a measurement temperature of 24° C. An example of a $^1$H-NMR chart is given in FIG. 1.

Figure 1:
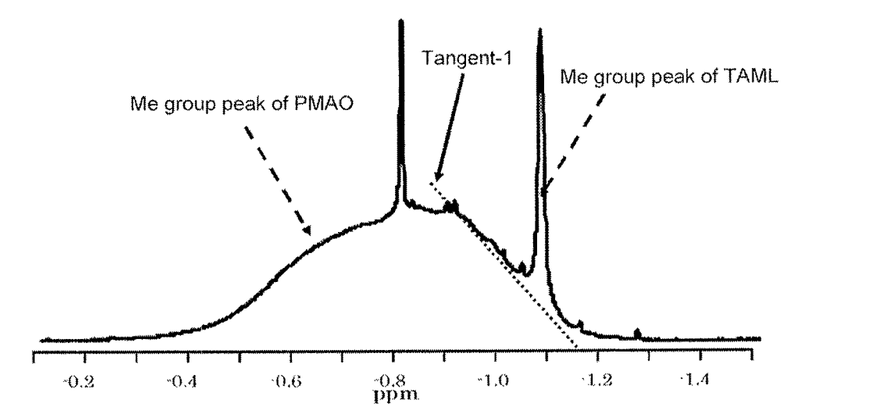
FIG. 1 An example of the $^1$H-NMR measurement results of a polymethylaluminoxane composition.

(i) The entire integral value of the Me group peak of polymethylaluminoxane containing trimethylaluminoxane that appeared from around −0.3 ppm to −1.2 ppm was determined. This was adopted as I (polymethylaluminoxane).

(ii) The Me group peak derived from TMAL in the vicinity of −1.1 ppm was cut out by means of tangent 1, and the integral value I (TMAL-Me) thereof was determined.

(iii) When the various integral values determined in (ii) were subtracted from the integral value I (polymethylaluminoxane) determined in (i), it became possible to determine the Me-group integral value I (PMAO-Me) of just the polymethylaluminum without the trimethylaluminum. When I (TMAL-Me) and I (PMAO-Me) were normalized by division by I (polymethylaluminoxane), it was possible to determine the mole fractions of Me(PMAO) and Me(TMAL).

The various peaks can be cut out conveniently by the method of using a commercial curve fitting program, the method of using baseline collection, and the like.

The analysis sample of the solution of polymethylaluminoxane composition was prepared by adding about 0.5 mL of $d_8$-THF to about 0.05 mL of the solution of polymethylaluminoxane composition. An analysis sample of solid polymethylaluminoxane composition was prepared by adding 0.5 mL of $d_8$-THF to 10 mg of a solution of polymethylaluminoxane.

The following reaction was conducted in a dry nitrogen gas atmosphere. The solvents employed were all dehydrated and degassed.

Preliminary Test 1 (benzoic acid-Al/O=1.20)

(1) Synthesis of a Solution of a Polymethylaluminoxane Composition

To a separable flask with stirrer and a 2 L internal volume were charged 240.8 g (3.34 mol) of trimethylaluminum (TMAL) and 600.5 g of toluene. The solution was cooled to 15° C. To this was slowly added 145.7 g (1.19 mol) of benzoic acid at a rate such that the temperature of the solution remained 25° C. or lower. Subsequently, the mixture was heated and aged for one hour at 50° C. At that time, the molar ratio of TMAL and benzoic acid oxygen atoms was 1.20. The reaction solution was heated for 32 hours at 70° C., and then heated for 6 hours at 60° C. to obtain a toluene solution of polymethylaluminoxane composition. The solution that was obtained was a transparent liquid without gel-like material. Aluminum analysis conducted after recovering the reaction solution revealed that the reaction yield indicated based on the aluminum atoms was quantitative. The aluminum concentration of the reaction solution obtained was 9.04 wt %. The Me(TMAL) quantity of the solution of polymethylaluminoxane composition obtained was determined by $^1$H-NMR to be 14.0 mol %. The solution of polymethylaluminoxane was in the form of a solution, so the solubility measurement described in the test method section was precluded. However, the concentration in toluene as calculated from the specific gravity of the solution and the aluminum concentration was about 3.0 mol/L.

(2) Evaluation of Ethylene Polymerization
Polymerization Conducted Using Bis(Cyclopentadienyl)Zirconium Dichloride To a 500 mL four-necked flask with magnetic stirrer was charged 250 mL of toluene and the toluene was heated to 34° C. To this were added 0.16 g (5.93 mmol) based on aluminum atoms of a toluene solution of polymethylaluminoxane, followed by bis(cyclopentadienyl)zirconium dichloride ($Cp_2ZrCl_2$) to achieve an Al/Zr molar ratio of 5000. Ethylene gas was blown in while heating the mixture to 40° C. Ten minutes later, the supplying of ethylene gas was stopped and methanol was introduced to deactivate the catalyst. The polyethylene produced was filtered and dried. The polymerization activity was determined to be $39 \times 10^6$ g-PE/mol-Zr·atm·hr. The molecular weight was 180,000 as measured by high temperature GPC, and the Mw/Mn was 2.9. The polymer was amorphous and there was pronounced fouling of the polymerization vessel.

Embodiment 1

(1) Synthesis of Solid Polymethylaluminoxane Composition

To a separable flask with stirrer and a 5 L internal volume were charged 406.5 g (1.361 mol-Al) of the toluene solution of polymethylaluminoxane composition prepared in Preliminary Test 1 (Al/O=1.20). Dry nitrogen was blown in through an inserted dip tube and nitrogen bubbling (250 mL/min) was conducted for 30 min with stirring. Subsequently, heating was conducted for 8 hours at 100° C. while stirring. Solid polymethylaluminoxane composition precipitated during the heating. The solution was cooled to 30° C. or lower, after which 3.6 L of n-hexane was added with stirring for washing. The solid polymethylaluminoxane composition was decanted, the supernatant was removed, and cleaning was conducted by decanting twice with 3 L of hexane. The solid obtained was dried under vacuum at room temperature to obtain polymethylaluminoxane in the form of a dry solid. The dry solid polymethylaluminoxane composition precipitation rate was 97% based on aluminum atoms of the solution of polymethylaluminoxane employed. The quantity of Me(TMAL) of the solid polymethylaluminoxane composition obtained was 9.2 mol % as determined by $^1$H-NMR.

(2) Analysis of Solid Polymethylaluminoxane Composition (a) Aluminum Content
The aluminum content of the dry solid polymethylaluminoxane composition was measured at 39.3 wt %-Al.
(b) Shape Evaluation
The particle diameter distribution of the dry solid polymethylaluminoxane composition was evaluated with a Master Sizer 2000 Hydro S, revealing a median diameter d(0.5) based on volume of 3.1 µm and a uniformity of 0.290.
(c) Measurement of Specific Surface Area
The specific surface area of the dry solid polymethylaluminoxane composition was measured, revealing a specific surface area per mmol of aluminum atoms of 20.1 $m^2$/mmol-Al.
(d) Proportion of Dissolution in Solvent
The proportions of dissolution in n-hexane and toluene of the dry solid polymethylaluminoxane composition were determined as 0.1 mol % and 0.35 mol %, respectively. These were extremely low values.

(3) Evaluation of Ethylene Polymerization

1. Polymerization Using Bis(Cyclopentadienyl)Zirconium Dichloride
To a 500 mL four-necked flask with magnetic stirrer was charged 250 mL of toluene and the toluene was heated to 34° C. To this was added 0.16 g (5.93 mmols) based on aluminum atom conversion of a toluene slurry solution of solid polymethylaluminoxane composition (Al/O=1.20). Bis(cyclopentadienyl)zirconium dichloride ($Cp_2ZrCl_2$) was added to achieve an Al/Zr molar ratio of 5000. Ethylene gas was blown in while heating the mixture to 40° C. Ten minutes later, the ethylene supply was stopped and methanol was introduced to deactivate the catalyst. The polyethylene that had been produced was filtered and dried. The polymerization activity was determined to be $68 \times 10^6$ g-PE/mol-Z·atm·hr.

The polymer obtained was in the form of free-flowing fine particles that did not adhere to the reaction vessel following polymerization. The molecular weight as determined by high-temperature GPC was 170,000 and the Mw/Mn was 2.6.

Embodiment 2

(1) Synthesis of Solid Polymethylaluminoxane Composition

With the exception that nitrogen bubbling (250 mL/min) was conducted for 60 min, a solid polymethylaluminoxane composition was prepared in the same manner as in Embodiment 1. The precipitation rate of the dry solid polymethylaluminoxane composition was 96.5% based on aluminum atoms of the solution of polymethylaluminoxane composition employed. The quantity of Me(TMAL) of the solid polymethylaluminoxane composition obtained was 9.1 mol % as measured by $^1$H-NMR.

(2) Analysis of the Solid Polymethylaluminoxane Composition (a) Aluminum Content
The aluminum content of the dry solid polymethylaluminoxane composition was measured at 40.3 wt %-Al.
(b) Shape Evaluation
The particle diameter distribution of the dry solid polymethylaluminoxane composition was evaluated with a Master Sizer 2000 Hydro S, revealing a median diameter d(0.5) based on volume of 1.5 µm and a uniformity of 0.300.
(c) Measurement of Specific Surface Area
The specific surface area of the dry solid polymethylaluminoxane composition was measured, revealing a specific surface area per mmol of aluminum atoms of 21.1 $m^2$/mmol-Al.
(d) Proportion of Dissolution in Solvent
The proportions of dissolution in n-hexane and toluene of the dry solid polymethylaluminoxane composition were determined as 0.1 mol % and 0.35 mol %, respectively. These were extremely low values.

(3) Evaluation of Ethylene Polymerization

1. Polymerization Using Bis(Cyclopentadienyl)Zirconium Dichloride
With the exception that the solid polymethylaluminoxane composition synthesized above was employed, polymerization was evaluated in the same manner as in (3) 1. of Embodiment 1 at $65 \times 10^6$ g-PE/mol-Z·atm·hr.

The polymer obtained was in the form of free-flowing fine particles that did not adhere to the reaction vessel following polymerization. The molecular weight as determined by high-temperature GPC was 170,000 and the Mw/Mn was 2.5.

Embodiment 3

(1) Synthesis of Solid Polymethylaluminoxane Composition

With the exception that nitrogen bubbling (5 mL/min) was conducted during solidification by heating, a solid polymethylaluminoxane composition was prepared in the same manner as in Embodiment 1. The precipitation rate of the dry solid polymethylaluminoxane composition was 97.5% based on aluminum atoms of the solution of polymethylaluminoxane composition employed. The quantity of Me(TMAL) of the solid polymethylaluminoxane composition obtained was 8.8 mol % as measured by $^1$H-NMR.

(2) Analysis of the Solid Polymethylaluminoxane Composition (a) Aluminum Content The aluminum content of the dry solid polymethylaluminoxane composition was measured at 40.3 wt %-Al.

(b) Shape Evaluation

The particle diameter distribution of the dry solid polymethylaluminoxane composition was evaluated with a Master Sizer 2000 Hydro S, revealing a median diameter d(0.5) based on volume of 0.9 μm and a uniformity of 0.310.

(c) Measurement of Specific Surface Area

The specific surface area of the dry solid polymethylaluminoxane composition was measured, revealing a specific surface area per mmol of aluminum atoms of 22.1 $m^2$/mmol-Al.

(d) Proportion of Dissolution in Solvent

The proportions of dissolution in n-hexane and toluene of the dry solid polymethylaluminoxane composition were determined as 0.1 mol % and 0.35 mol %, respectively. These were extremely low values.

(3) Evaluation of Ethylene Polymerization

1. Polymerization Using Bis(Cyclopentadienyl)Zirconium Dichloride

With the exception that the solid polymethylaluminoxane composition synthesized above was employed, polymerization was evaluated in the same manner as in (3) 1. of Embodiment 1 at 66×$10^6$ g-PE/mol-Z·atm·hr.

The polymer obtained was in the form of free-flowing fine particles that did not adhere to the reaction vessel following polymerization. The molecular weight as determined by high-temperature GPC was 170,000 and the Mw/Mn was 2.5.

Embodiment 4

(1) Synthesis of Solid Polymethylaluminoxane Composition

With the exception that nitrogen bubbling (7.5 mL/min) was conducted during solidification by heating, a solid polymethylaluminoxane composition was prepared in the same manner as in Embodiment 1. The precipitation rate of the dry solid polymethylaluminoxane composition was 98.5% based on aluminum atoms of the solution of polymethylaluminoxane composition employed. The quantity of Me(TMAL) of the solid polymethylaluminoxane composition obtained was 8.2 mol % as measured by $^1$H-NMR.

(2) Analysis of the Solid Polymethylaluminoxane Composition (a) Aluminum Content The aluminum content of the dry solid polymethylaluminoxane composition was measured at 42.1 wt %-Al.

(b) Shape Evaluation

The particle diameter distribution of the dry solid polymethylaluminoxane composition was evaluated with a Master Sizer 2000 Hydro S, revealing a median diameter d(0.5) based on volume of 0.7 μm and a uniformity of 0.300.

(c) Measurement of Specific Surface Area

The specific surface area of the dry solid polymethylaluminoxane composition was measured, revealing a specific surface area per mmol of aluminum atoms of 21.5 $m^2$/mmol-Al.

(d) Proportion of Dissolution in Solvent

The proportions of dissolution in n-hexane and toluene of the dry solid polymethylaluminoxane composition were determined as 0.1 mol % and 0.35 mol %, respectively. These were extremely low values.

(3) Evaluation of Ethylene Polymerization

1. Polymerization Using Bis(Cyclopentadienyl)Zirconium Dichloride

With the exception that the solid polymethylaluminoxane composition synthesized above was employed, polymerization was evaluated in the same manner as in (3) 1. of Embodiment 1 at 72×$10^6$ g-PE/mol-Z·atm·hr.

The polymer obtained was in the form of free-flowing fine particles that did not adhere to the reaction vessel following polymerization. The molecular weight as determined by high-temperature GPC was 200,000 and the Mw/Mn was 2.4.

2. Polymerization Using Bisindenylzirconium Dichloride

To a glass flask equipped with stirrer was charged 10 g (155.9 mmol-Al) of the solid polymethylaluminoxane composition synthesized above and a slurry concentration of 15 wt % was prepared with toluene. To this was gradually added at room temperature a toluene solution of bisindenylzirconium dichloride (made by Wako Chemicals, 0.78 mmol-Zr) and the mixture was reacted with stirring for 3 hours at that temperature. Since no coloration of the supernatant was seen, cleaning was not conducted. Ethylene homopolymerization was conducted using the toluene slurry of the catalyst that had been prepared.

To an SUS autoclave (1,500 mL) with pressure gauge and stirrer made of pressure-resistant glass was charged 800 mL of hexane. Four rounds of ethylene 0.5 MPa pressurization/depressurization were conducted to purge nitrogen gas from the system. Subsequently, 0.5 mol/L of a hexane solution of triethylaluminum was added. The internal solution was heated to 65° C. in an oil bath. The toluene slurry of the catalyst prepared above (15 mg of solid catalyst) was added under pressure, and immediately, the pressure within the system was increased to 0.7 MPa with ethylene and polymerization was begun. The internal pressure of the system was kept at 0.7 MPa and the polymerization temperature at 70° C. Slurry polymerization was conducted for one hour. Following an hour of polymerization, the ethylene supply was cut off and the gas within the system was released to halt polymerization. Methanol containing a small quantity of di-t-butyl-hydroxytoluene was added, and the polymer was filtered out with a Nutsche. When the polymer obtained was dried under reduced pressure at 50° C., the weight of the polymer was 350 g and the polymerization activity was about 23,300 g-PE/g-cat·hr. This was extremely high activity. The polymer obtained was in the form of fine free-flowing particles and did not adhere to the reaction vessel following polymerization.

Embodiment 5

(3) Evaluation of Ethylene Polymerization

2. Polymerization Using Bisindenylzirconium Dichloride

With the exception that the solid polymethylaluminoxane composition obtained in Embodiment 1 was employed, a catalyst was prepared by the same method as that described in (3) 2. of Embodiment 4. Polymerization by the catalyst obtained was evaluated, yielding 250 g of polymer. The polymerization activity was about 16,700 g-PE/g-cat·hr. This was extremely high activity. The polymer obtained was in the form of fine free-flowing particles and did not adhere to the reaction vessel following polymerization.

Embodiment 6

(3) Evaluation of Ethylene Polymerization

2. Polymerization Using Bisindenylzirconium Dichloride

With the exception that the solid polymethylaluminoxane composition obtained in Embodiment 2 was employed, a catalyst was prepared by the same method as that described in (3) 2. of Embodiment 4. Polymerization by the catalyst obtained was evaluated, yielding 285 g of polymer. The polymerization activity was 19,000 g-PE/g-cat·hr. This was extremely high activity. The polymer obtained was in the form of fine free-flowing particles and did not adhere to the reaction vessel following polymerization.

Embodiment 7

(3) Evaluation of Ethylene Polymerization

2. Polymerization Using Bisindenylzirconium Dichloride

With the exception that the solid polymethylaluminoxane composition obtained in Embodiment 3 was employed, a catalyst was prepared by the same method as that described in (3) 2. of Embodiment 4. Polymerization by the catalyst obtained was evaluated, yielding 312 g of polymer. The polymerization activity was 20,800 g-PE/g-cat·hr. This was extremely high activity. The polymer obtained was in the form of fine free-flowing particles and did not adhere to the reaction vessel following polymerization.

Comparative Example 1

The present comparative example is a replication of Embodiment 7 of Patent Reference 7.
(1) Synthesis of a Solution of a Polymethylaluminoxane Composition To a separable flask with stirrer and an internal volume of 500 mL were charged 68.39 g (948.81 mmol) of trimethylaluminum (TMAL) and 102.51 g of toluene. The solution was cooled to 15° C. A solution of 82.13 g (683.56 mmol) of acetophenone and 19.35 g of toluene was slowly added at a rate such that the internal temperature within the flask remained 25° C. or less. Heating and aging were then conducted for an hour at 50° C. At the time, the molar ratio of TMAL and acetophenone oxygen atoms was 1.39. Using the toluene solution of the polymethylaluminoxane composition prepared in Preliminary Test 1 as an activation agent for a thermal decomposition reaction, a quantity of 49.0 mmol based on aluminum atoms was introduced all at once to the reaction solution. Subsequently, the mixture was heated for 9 hours at 65° C. to obtain a toluene solution of the polymethylaluminoxane composition using acetophenone as an oxygen source. The solution obtained was a pale yellow, transparent liquid without gel-like material. Aluminum concentration analysis was conducted after recovering the reaction solution, revealing that the reaction yield indicated based on aluminum atoms was quantitative. The aluminum concentration of the reaction solution obtained was 9.15 wt %. The quantity of Me(TMAL) of the solution of polymethylaluminoxane composition obtained was 23.2 mol % as measured by $^1$H-NMR. Since the solution of polymethylaluminoxane composition was in the form of a solution, it was impossible to measure the solubility as described in the section on test methods. However, the concentration in toluene as calculated from the specific gravity and aluminum concentration of the solution was about 3.1 mol/L.

(2) Evaluation of Ethylene Polymerization

Polymerization evaluation was conducted by the same method as that described in (2) 1. of Preliminary Test 1, revealing a polymerization activity of $65 \times 10^6$ g-PE/mol-Z·atm·hr. The polymer was amorphous in shape and fouling of the polymerization vessel was pronounced.

(3) Synthesis of Solid Polymethylaluminoxane Composition

With the exceptions that the solution of polymethylaluminoxane composition prepared using the above acetophenone was employed and nitrogen bubbling was not conducted, a solid polymethylaluminoxane composition was prepared in the same manner as in Embodiment 1. The precipitation rate of the dry solid was 54.8% based on the aluminum atoms of the solution of polymethylaluminoxane composition employed. The quantity of Me(TMAL) of the solid polymethylaluminoxane composition obtained was 11.8 mol % as measured by $^1$H-NMR.

(4) Analysis of the Solid Polymethylaluminoxane Composition (a) Aluminum Content The aluminum content of the dry solid polymethylaluminoxane composition was measured at 40.1 wt %-Al.

(b) Shape Evaluation

The particle diameter distribution of the dry solid polymethylaluminoxane composition was evaluated with a Master Sizer 2000 Hydro S, revealing a median diameter d(0.5) based on volume of 6.2 µm and a uniformity of 0.300.

(c) Measurement of Specific Surface Area

The specific surface area of the dry solid polymethylaluminoxane composition was measured, revealing a specific surface area per mmol of aluminum atoms of 13.2 m$^2$/mmol-Al.

(5) Evaluation of Ethylene Polymerization

With the exception that the solid polymethylaluminoxane composition synthesized above was employed, polymerization evaluation was conducted by the same method as that described in (3) 1. of Embodiment 1, revealing a polymerization activity of $37 \times 10^6$ g-PE/mol-Z·atm·hr. The polymer obtained was in the form of fine free-flowing particles and did not adhere to the reaction vessel following polymerization.

2. Polymerization Using Bisindenylzirconium Dichloride

With the exception that the solid polymethylaluminoxane composition synthesized above was employed, a catalyst was prepared by the same method as that described in (3) 2. of Embodiment 4. Evaluation of the polymerization of the catalyst obtained revealed that 23 g of polymer was obtained. The polymerization activity was about 1,500 g-PE/g-cat·hr. The polymer obtained was in the form of fine free-flowing particles and did not adhere to the reaction vessel following polymerization.

Comparative Example 2

This comparative example is a replication of Embodiment 1 in Patent Reference 7.
(1) Synthesis of Solid Polymethylaluminoxane Composition To a separable flask with stirrer and a 5 L internal volume was charged 406.5 g (1.361 mol-Al) of a toluene solution of the polymethylaluminoxane composition prepared in Preliminary Test 1 (Al/O=1.20) and the mixture was heated for 8 hours at 100° C. with stirring. The solid polymethylaluminoxane composition precipitated out during heating. The solution was cooled to 30° C. or lower, and 3.6 L of n-hexane was added with stirring for cleaning. The solid polymethylaluminoxane composition was decanted, the supernatant was removed, and two rounds of decantation with 3 L of n-hexane were conducted for cleaning. The solid obtained was dried under reduced pressure at room temperature to obtain a dry solid polymethylaluminoxane composition. The precipitation rate of the dry solid polymethylaluminoxane composition obtained was 96% based on the aluminum atoms of the solution of polymethylaluminoxane composition employed. The quantity of Me(TMAL) of the solid polymethylaluminoxane composition obtained was 9.0 mol % as measured by $^1$H-NMR.
(2) Analysis of the Solid Polymethylaluminoxane Composition
(a) Aluminum Content The aluminum content of the dry solid polymethylaluminoxane composition was measured at 37.3 wt %-Al.
(b) Shape Evaluation The particle diameter distribution of the dry solid polymethylaluminoxane composition was evaluated with a Master Sizer 2000 Hydro S, revealing a median diameter d(0.5) based on volume of 9.4 μm and a uniformity of 0.296.
(c) Measurement of Specific Surface Area The specific surface area of the dry solid polymethylaluminoxane composition was measured, revealing a specific surface area per mmol of aluminum atoms of 19.5 m$^2$/mmol-Al.
(d) Proportion of Dissolution in Solvent The proportions of dissolution in n-hexane and toluene of the dry solid polymethylaluminoxane composition were determined as 0.1 mol % and 0.4 mol %, respectively. These were extremely low values.
(3) Evaluation of Ethylene Polymerization
1. Polymerization Using Bis(Cyclopentadienyl)Zirconium Dichloride To a 500 mL four-necked flask with magnetic stirrer was charged 250 mL of toluene and the toluene was heated to 34° C. To this was added 0.16 g (5.93 mmol) based on aluminum atom conversion of a toluene slurry solution of the solid polymethylaluminoxane composition (Al/O=1.20). Bis(cycholpentadienyl)zirconium dichloride (Cp$_2$ZrCl$_2$) was added to achieve an Al/Zr molar ratio of 5,000. Ethylene gas was blown in while heating the mixture to 40° C. Ten minutes later, the ethylene gas supply was halted and methanol was introduced to deactivate the catalyst. The polyethylene that had been produced was filtered and dried. The polymerization activity was determined to be 64×10$^6$ g-PE/mol-Zr·atm·hr.

The polymer obtained was in the form of fine free-flowing particles that did not adhere to the reaction vessel following polymerization. The molecular weight was 160,000 as determined by high temperature GPC, and Mw/Mn was 2.7.

2. Polymerization Using Bisindenylzirconium Dichloride

With the exception that the solid polymethylaluminoxane composition obtained above was employed, a catalyst was prepared by the same method as that described in (3) 2. of Embodiment 4. Evaluation of the polymerization of the catalyst obtained revealed that 80 g of polymer was obtained. The polymerization activity was about 5,300 g-PE/g-cat·hr. The polymer obtained was in the form of fine free-flowing particles and did not adhere to the reaction vessel following polymerization.

The results of Embodiments 1 to 7 and Comparative Examples 1 and 2 are collectively given in the following table.

TABLE 1

| Embodiment | Median diameter based on volume (μm) | Evaluation of ethylene polymerization | |
|---|---|---|---|
| | | (*10$^6$ g-PE/ mol-Zr·atm·hr) [1] | (g-PE/ g-cat·hr) [2] |
| 1 | 3.1 | 68 | — |
| 2 | 1.5 | 65 | — |
| 3 | 0.9 | 66 | — |
| 4 | 0.7 | 72 | 23,300 |
| 5 | 3.1 | — | 16,700 |
| 6 | 1.5 | — | 19,000 |
| 7 | 0.9 | — | 20,800 |
| Comp. Ex. 1 | 6.2 | 37 | 1,500 |
| Comp. Ex. 2 | 9.4 | 64 | 5,300 |

[1] Employed with the addition of bis(cyclopentadienyl)zirconium dichloride
[2] Employed with the addition of bisindenylzirconium dichloride

INDUSTRIAL APPLICABILITY

The present invention is useful in the technical field of manufacturing olefin polymers.

The invention claimed is:

1. A solid polymethylaluminoxane composition comprising polymethylaluminoxane and trimethylaluminum:
   (i) wherein an aluminum content of the composition falls within a range of 36 mass % to 43 mass %;
   (ii) wherein a mole fraction of methyl groups derived from the trimethylaluminum relative to the total number of moles of methyl groups in the composition is 12 mol % or less; and
   (iii) wherein the composition is particulate and has a median diameter based on volume falling within a range of 0.1 μm to less than 5 μm.

2. The composition according to claim 1, wherein:
   the solubility in n-hexane at 25° C. is 0 to 2 mol %; and
   the solubility in toluene at 25° C. is 0 to 2 mol %.

3. The composition according to claim 1, wherein the uniformity as given by the following formula is 0.45 or lower:

uniformity=$\Sigma Xi|d(0.5)-Di|/d(0.5)\Sigma Xi$ (wherein Xi denotes the volume percentage of a particle i of solid aluminoxane composition in a particle diameter distribution histogram, d(0.5) denotes the median diameter based on volume in the histogram, and Di denotes the diameter based on volume of particle i in the histogram).

4. The composition of claim 1, wherein the specific surface area falls within a range of 10 to 25 m$^2$/mmol-Al.

5. The composition according to claim 1, comprising trimethyl aluminum and polymethylaluminoxane containing the unit denoted by general formula (I) below:

-[(Me)AlO]$_n$—  (I)

wherein n denotes an integer of 10 to 50.

6. The composition according to claim 1, not containing $SiO_2$.

7. A method for manufacturing the solid polymethylaluminoxane composition according to claim 1, comprising a step (a) of heating an aromatic hydrocarbon solution containing trimethylaluminum and the polymethylaluminoxane containing the unit denoted by general formula (II) below (referred to hereinafter as the solution of polymethylaluminoxane composition) to cause solid polymethylaluminoxane composition containing trimethylaluminum and polymethylaluminoxane to precipitate;

wherein prior to step (a), a dry, inert gas is bubbled through the solution of polymethylaluminoxane composition, and/or during at least a portion of the period of step (a), a dry, inert gas is bubbled through the solution of polymethylaluminoxane composition:

$$-[(Me)AlO]_n- \quad (II)$$

wherein n denotes an integer of 1 to 50.

8. The manufacturing method according to claim 7, wherein in the solution of polymethylaluminoxane composition prior to heating, the mole fraction of methyl groups derived from trimethylaluminum moieties relative to the total number of mols of methyl groups is 15 mol% or less.

9. The manufacturing method according to claim 7, wherein in step (a), a suitable heating temperature and heating period are selected from:
(i) heating temperatures falling within a range of 80 to 200° C. and
(ii) heating periods of from 5 minutes or more to less than 24 hours, to cause the solid polymethylaluminoxane composition to precipitate.

10. The manufacturing method according to claim 7, wherein the solution of polymethylaluminoxane composition employed as a starting material in step (a) is obtained by thermally decomposing an alkyl aluminum compound having an aluminum-oxygen-carbon bond.

11. The manufacturing method according to claim 10, wherein the alkyl aluminum compound having aluminum-oxygen-carbon bond is prepared by reacting trimethylaluminum and an oxygen-containing organic compound.

12. The manufacturing method according to claim 11, wherein the oxygen-containing organic compound is an aliphatic or aromatic carboxylic acid denoted by general formula (III):

$$R^1\text{-}(COOH)_n \quad (III)$$

wherein $R^1$ denotes a hydrocarbon group in the form of a C1 to C20 linear or branched alkyl group, alkenyl group, or aryl group and n denotes an integer of 1 to 5.

13. The manufacturing method according to claim 11, wherein the reaction of the trimethylaluminum and oxygen-containing organic compound is conducted such that the molar ratio of aluminum atoms contained in the trimethylaluminum and oxygen atoms contained in the oxygen-containing compound falls within a range of 1.15 to 1.4:1.

14. An olefin polymerization catalyst comprising the solid polymethylaluminoxane composition according to claim 1 and a catalyst component in the form of the transition metal compounds denoted by general formula (IV) below:

$$MR^5R^6R^7R^8 \quad (IV)$$

wherein M denotes a transition metal element; $R^5$, $R^6$, $R^7$, and $R^8$ denote together organic groups comprising one or two cycloalkanedienyl skeletons, or each independently denote an organic group or atom selected from the group consisting of a hydrocarbon group with 1 to 20 carbon atoms, alkoxy group, aryloxy group, alkylsilyl group, alkylamide group, alkylimide group, alkylamino group, alkylimino group, hydrogen atom, and halogen atom.

15. A method for manufacturing a polyolefin, comprising polymerizing an olefin using the catalyst according to claim 14.

* * * * *